Figure 1:
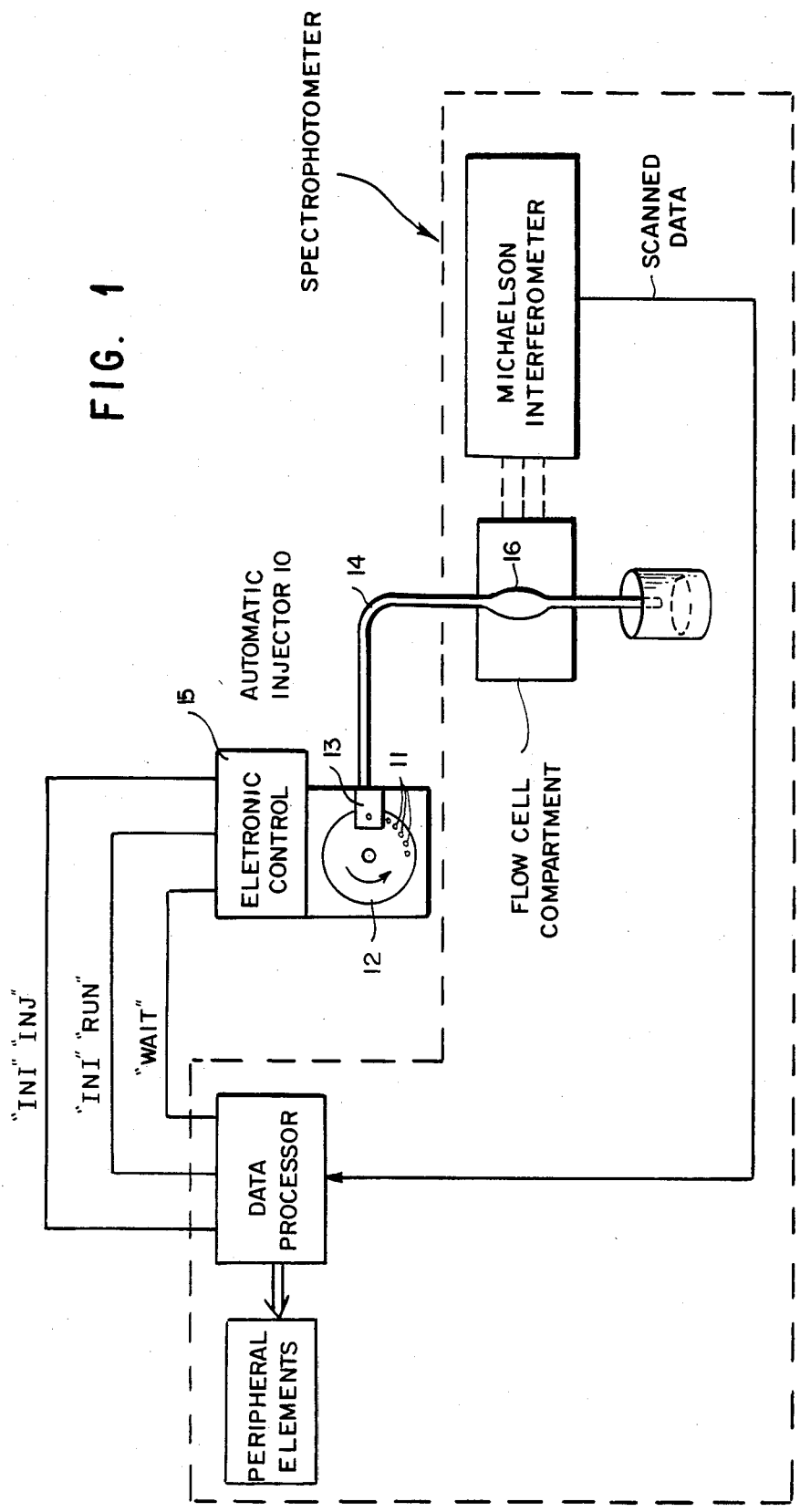

United States Patent [19]

Inman, Jr. et al.

[11] Patent Number: 4,733,965

[45] Date of Patent: Mar. 29, 1988

[54] AUTOMATED SYSTEM FOR SPECTRO-PHOTOMETRIC ANALYSIS OF LIQUIDS

[75] Inventors: Guy W. Inman, Jr., Greenville; Charles H. Powell, Jr., Winterville; Guy W. Martin, Jr., Chapel Hill, all of N.C.

[73] Assignee: Burroughs Wellcome Co., Research Triangle Park, N.C.

[21] Appl. No.: 490,179

[22] Filed: Apr. 29, 1983

Related U.S. Application Data

[63] Continuation of Ser. No. 205,621, Nov. 10, 1980, abandoned.

[51] Int. Cl.$^4$ .............................................. G01J 3/42
[52] U.S. Cl. ................... 356/326; 73/864.21; 356/346; 364/498
[58] Field of Search ............... 364/498; 422/63, 64, 422/65, 81; 73/864.21; 356/319, 326, 328, 323–325, 346, 300

[56] References Cited

U.S. PATENT DOCUMENTS

| | | | |
|---|---|---|---|
| 3,257,562 | 6/1966 | Erdman et al. | 356/325 |
| 3,550,453 | 12/1970 | Lightner et al. | 73/864.21 X |
| 3,842,679 | 10/1974 | Iwao et al. | 73/864.21 |
| 4,176,957 | 12/1979 | Maeda et al. | 356/319 |
| 4,311,484 | 1/1982 | Fosslien | 73/864.21 |

Primary Examiner—F. L. Evans
Attorney, Agent, or Firm—Robert F. O'Connell

[57] ABSTRACT

A system for providing a spectrophotometric analysis of a plurality of fluid samples, the system including a spectrophotometer having a low pressure flow cell and an automatic injector device which stores the fluid samples without exposure to the atmosphere and injects the samples successively at low pressure into the flow cell where they can be scanned to produce scanned data for processing. The system prevents the scanning of each fluid sample until the injection thereof has been completed, the processing of scanned data for each fluid sample being performed substantially simultaneously with the injection of the next successive fluid sample into the flow cell.

9 Claims, 4 Drawing Figures

AUTOMATED SYSTEM FOR SPECTRO-PHOTOMETRIC ANALYSIS OF LIQUIDS

This is a continuation of application Ser. No. 205,621 filed Nov. 10, 1980, now abandoned.

INTRODUCTION

This invention relates generally to spectrophometric analyses of fluid samples and, more particularly, to automated techniques for performing spectrophotometric analyses of a plurality of fluid samples.

BACKGROUND OF THE INVENTION

Apparatus for providing spectrum analyses using photodetection devices, such apparatus generally being referred to as spectrophotometers, have long been used to analyze fluid samples by comparing the spectral characteristics of unknown fluid samples, over selected frequency bands, with the spectral characteristics of known standard fluid samples. One apparatus which has been available and has been successfully used for such purpose, for example, is the Nicolet Model 7199 Fourier Transform Infrared Spectrophotometer made and sold by Nicolet Instrument Corporation of Madison, Wisconsin, which spectrophotometer utilizes Fourier transform techniques for analyzing materials in the infrared portion of the spectrum.

In using such an instrument for analysis of fluids a container is normally filled manually with said fluid, whether of a blank solution, a known standard solution, or an unknown fluid sample solution, to be analyzed. The fluid is then appropriately scanned to provide scanned data with respect to its spectral characteristics and the scanned data is then suitably processed using Fourier transform techniques, as would be well known to those in the art. During the filling of the container the fluid sample is generally exposed to the atmosphere. When the analysis of a particular fluid sample has been completed, the container must be removed, rinsed clean and dried before being filled with another fluid solution and replaced in the apparatus for analysis of the next fluid sample.

Such a technique not only is physically cumbersome but requires the presence of an operator for performing each container loading, cleaning, refilling and replacement operation. Further, the time required to perform an analysis of a large number of different fluid samples becomes undesirably excessive and, since the user's presence is required throughout the overall operation, the user is not free to perform other tasks. Moreover, the exposure to the atmosphere of the fluid samples during the filling and scanning process causes fluid evaporation to occur, particularly when the fluid is relatively highly volatile in nature.

It is desirable then that a technique be devised for performing a spectrophotometric analysis of a relatively large number of different fluid samples in an automated fashion so as to decrease the overall time involved therefor and to free up the user for other tasks while the consecutive sampling and analyses of the samples are being performed, as well as to free up the instrument itself for other analytic tasks. It is further desirable that such automated technique be arranged to avoid the necessity for removing the container in which the fluid sample is retained so that accuracy and precision are increased and instrument purging thereof remains constant. It is further desirable that the fluid samples be handled so that little or no evaporation thereof occurs.

BRIEF SUMMARY OF THE INVENTION

The technique of the invention produces the above advantages by providing for the appropriate use of an automatic fluid injection device with a spectrophotometer, such as a Fourier Transform Infrared (FTIR) apparatus, for example. One presently available exemplary automatic fluid injection device that has been found to be adaptable for use in accordance with the invention is the Model 725 Automatic Injector made and sold by Micromeritics Instrument Company of Norcross, Ga. Such device provides for the availability of up to sixty four separate fluid samples, e.g., liquid solutions, including blank solutions, known standard solutions, and unknown sample solutions, each solution being contained in separate hermetically sealed glass vials. Such device has heretofore normally been used only for the injection of liquid samples into a high pressure liquid chromatograph (HPLC) and, accordingly, it has conventionally been required that the device be used with a suitable high pressure valve and pump system which permits consecutive samples to be supplied at high pressures (normally within a range from about 1000 psi up to as high as about 7000 psi) to the HPLC. Up to now, however, no one has considered, and no one has devised a technique for, using such an injection device with a spectrophotometer.

This invention provides for the successful adaptation of an automatic liquid injection device, such as the aforementioned Micromeritics Model 725 Automatic Injector, in combination with a spectrophotometer, such as the aforementioned Nicolet 7199 spectrophotometer. In accordance therewith, the overall system, first of all, eliminates the high pressure valve and pump system normally used with the Model 725 Automatic Injector and provides a system and method for using the aforesaid novel combination in a manner which permits the automatic injection of a plurality of successive fluid samples for scanning and subsequent analysis thereof. Appropriate control of the steps required for such process is provided so that the injection of snmples and the scanning and analysis of each can be successfully coordinated. Thus, suitable techniques are devised to coordinate the sequencing of the entry of desired parameter values for controlling the operation of the spectrophotometer, the injection of blank solutions, standard solutions and sample (unknown) solutions, the scanning thereof, and the data processing analysis thereof, as well as the appropriate display of the processed information.

In accordance therewith, a low pressure flow cell is used in the spectrophotometer and the fluid samples are directly injected at low pressure into the flow cell without exposure to the atmosphere. The scanning operation is controlled so as to be prevented from occurring until the injection of the fluid sample has been completed. During the injection of the next successive fluid sample, processing of the previously injected fluid sample can occur substantially simultaneously.

DESCRIPTION OF THE INVENTION

Figure 2:
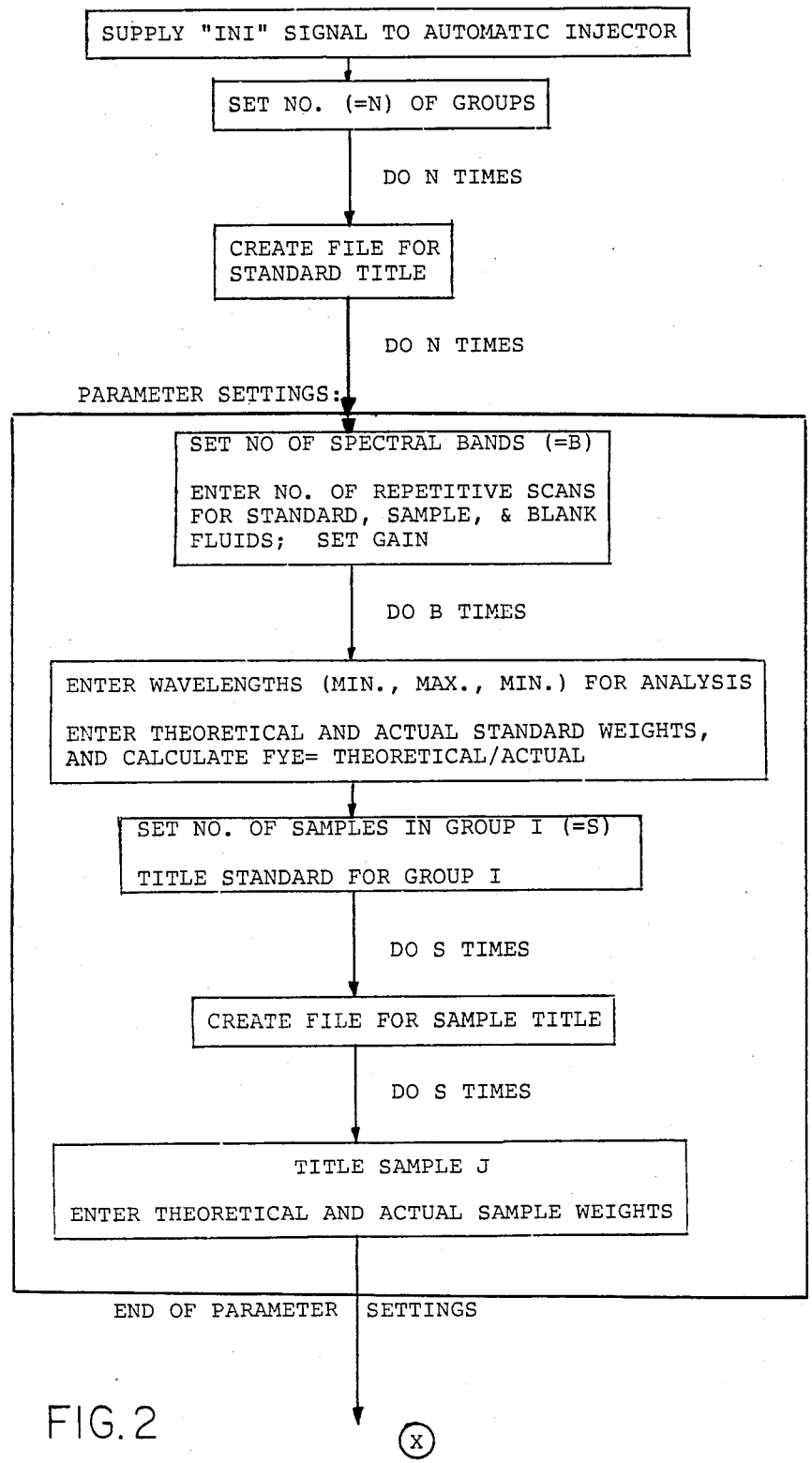
Figure 2A:
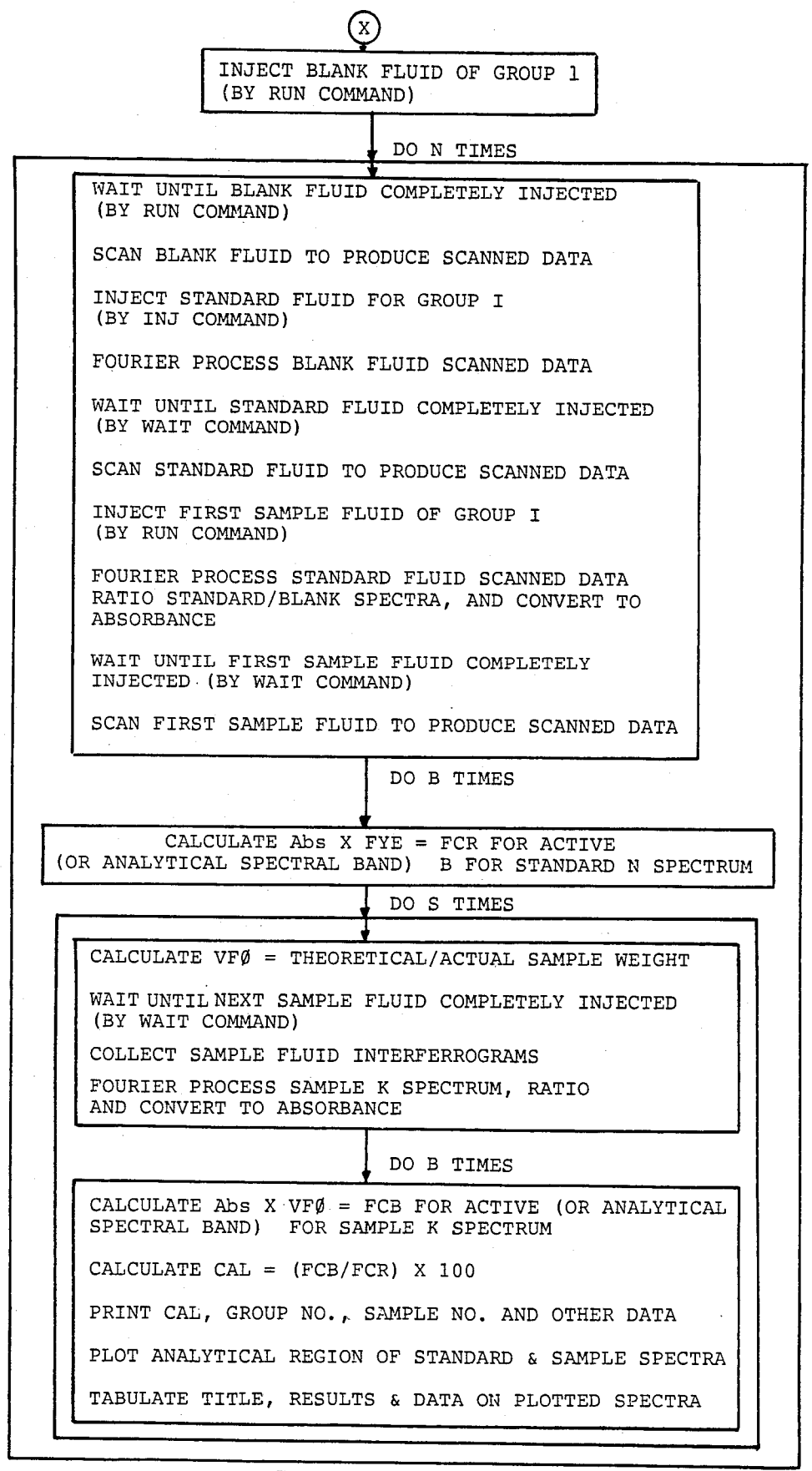
Figure 3:
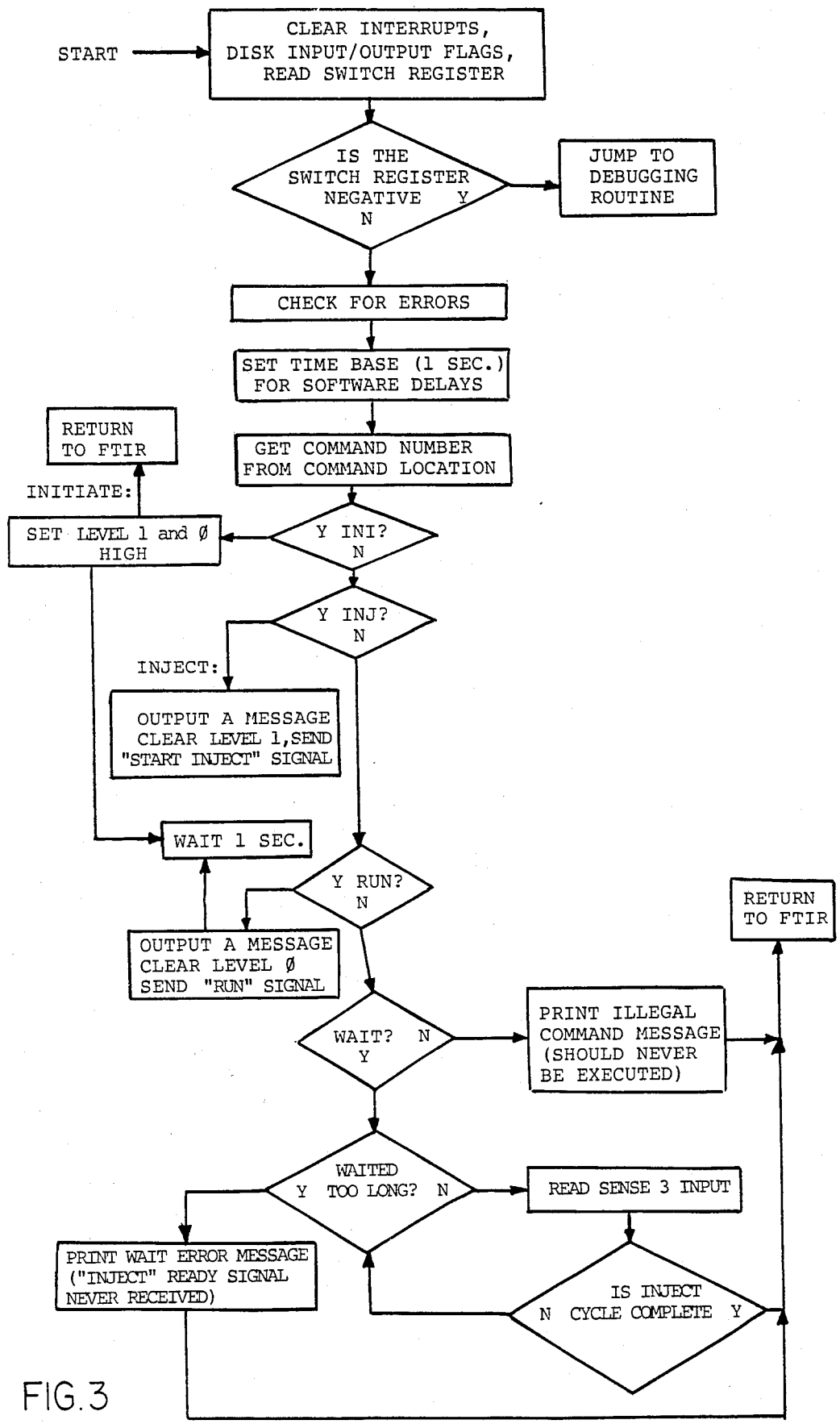

The invention can be described in more detail with the help of the accompanying drawings wherein FIG. 1 shows a simplified block diagram of a particular embodiment of the invention;

FIGS. 2 and 2A show a flow chart for setting parameter values and performing the required scanning and analyses in accordance with the invention; and FIG. 3 shows a flow chart of the stages performed by the device of the invention in response to INJ, RUN and WAIT commands.

As can be seen in FIG. 1, an automatic injection device 10, such as the aforementioned Model 725 Automatic Injector made by Micromeritics Instrument Corporation, is arranged to provide successive samples of fluids from a plurality of separate capped vials 11 mounted on a rotating turntable 12. Since such device has been generally available to the art, the specific structure thereof is already known and need not be described in more detail other than as represented here in diagrammatic fashion. As is known, the hermetically sealed vials or capsules containing the fluid samples to be injected into an associated analytical instrument is moved into alignment with an injection needle assembly 13, whereupon the fluid in the vial is forced under relatively low pressure into a flow line 14. Electronic control circuitry 15 controls the movement of the turntable and actuates the needle injection assembly, as required and as is known with respect to the Model 725 instrument.

Normally, the injection device is used with a device operating under high pressures, such as an HPLC, wherein the sample fluid is supplied to a high pressure pump and valve system so that the fluid can be in turn supplied at the required high pressure to the HPLC.

However, in the embodiment of the invention as described herein, the automatic injector is adapted to supply successive fluid samples to a flow cell 16 which is located in a cell compartment of a spectrophotometer, such as the aforementioned Nicolet Model 7199 FTIR spectrophotometer.

Unlike previously known uses of such automatic injector, no high pressure pump and valve interface unit is required and the fluid samples can be supplied directly at low pressure to the low pressure flow cell 16 via flow line 14. During the flow of the fluid from the vial to the flow cell, the pressure may be slightly higher than atmospheric pressure. Once the loading of the flow cell is completed the fluid system is substantially at atmospheric pressure.

When the fluid has been supplied to flow cell 16 and the injection process has been completed, the fluid sample can be scanned and analyzed in accordance with normal well known techniques used in the FTIR apparatus. Excess fluid supplied from the automatic injector device (each of the vials normally can contain an amount of fluid greater than the capacity of the flow cell) and sampled fluid which has been scanned and analyzed and is replaced by the next successive fluid sample can be discarded as waste product, as shown.

In order to assure that the supply of fluid samples by the automatic injector device 10 is correctly coordinated with the scanning and analysis operation of the FTIR apparatus, a method of operation has been devised in accordance with the invention. Such method can be best explained with the help of the flow charts depicted in FIGS. 2, 2A and 3. While such method can be embodied in appropriate hardware logic circuitry, firmware, or as software in a suitable data processor, it is most efficient to embody such method by using the data processor which is already available as part of the FTIR apparatus, or by using a separate microprocessor, for example, as would be within the skill of the art once the unique method is described as shown in FIGS. 2, 2A and 3. The Nicolet Model 7199 instrument has, for example, a data processor portion (normally identified as the Nicolet Model 1180 Computer) which can be used for such purpose as well as for its conventional purpose of controlling the scanning and Fourier transform anaylsis operations.

As can be seen in FIGS. 2 and 2A, the desired parameters for the analysis of a plurality of fluid samples must be set. Prior thereto, however, the interface signals, at the external I/O port of the Model 1180 computer, for starting the injection operation most be initially set to a state (in the particular embodiment described herein such state can be a "high" state) which prevents the initiation of any injection operation by the Model 725 device while such desired parameters are being set. For this purpose an "initialize" command signal ("INI") is provided by the Model 1180 computer so that the internal signals of the Model 1180 computer which supply the injection start signals for the automatic injector (identified as Level 1 and Level $\phi$ signals as the corresponding I/O ports) are set to their "high" states. So long as such signals are "high", fluid injection is prevented from occurring until a suitable injection command (either an "INJ" or "RUN" command, as described below) is supplied. The parameters can then be set as follows.

The number of groups of fluid samples is identified by the user. Each group of samples requires the use of a blank solution, that is, a solution which does not contain the material to be analyzed but only the solvent which is utilized in conjunction with the material to be analyzed. The spectral characteristics of the blank solution are determined so that they can subsequently be eliminated (i.e., "subtracted out") from the spectral characteristics of the fluid samples to be analyzed, as is well known to the art. Each group further requires the use of a known standard fluid, the spectral characteristics of which are known. The characteristics of such fluid are used as the standard against which one or more unknown fluid samples are to be compared. Each group also comprises one or more unknown fluid samples, the spectral characteristics of each of which are to be compared to the standard fluid sample which is being used for the entire group. In the particular embodiment being described, for example, the Model 725 injector turntable can store up to 64 vials which comprise the blank, standard and sample fluids of the selected number of groups which are to be analyzed.

A memory storage file (i.e., stored data) is created for the standard titles which are to be used in plotting the results of the analysis, as is known to those in the art when using spectrophotometric devices, such as the Nicolet Model 7199 apparatus discussed here. The remaining parameter setting steps, for example, can identify the number of samples in each group, the number of scans to be made for each sample, the number of components (or IR frequency bands) to be analyzed for the samples in each group, the analytical wavelengths for each component (or IR band), and the theoretical and actual weights of the standards and samples involved.

Once the above parameters are set, the initial injection command is supplied by the Model 1180 computer to the automatic injection device to inject the blank solution which is being used for the first group of samples. In the particular embodiment being described, the injection operation begins when the vial containing the blank solution of the first group is aligned with the needle assembly, at which state the needle of te needle assembly 13 must be in its "up" position. When the needle is in an "up" position, a RUN command signal is required to start the injection of the blank solution from the first vial. Subsequently, after each injection operation the needle is left in its "down" position and a different command signal, i.e., an INJ command signal, must be used for the Model 725 device. Accordingly, since the needle is initially in an "up" position for the blank solution of the first group, the RUN command signal is supplied to the injector to start the injection of such blank fluid.

When the injection has been initiated, a WAIT command signal is supplied from the injector device to the Model 1180 computer to prevent the scanning operation from starting until the injection cycle has been completed, as explained more fully with reference to FIG. 3. The scanning of the blank solution provides the required scanned data in accordance with the conventional operation of the Model 7199 apparatus.

An INJ command signal is then supplied to the injector to load the flow cell with the known standard fluid from the next vial. A Fourier transform analysis of the previously injected blank solution can then be performed by the Model 7199 apparatus substantially simultaneously with the injection of the standard fluid from the next successive vial. The scanning operation with respect to the next successive standard fluid, however, is prevented from occurring by another WAIT command signal, until the injection of the standard fluid into the flow cell has been completed.

Scanning of the standard fluid is often performed and, while the first unknown fluid of the first group is being injected into the flow cell, appropriate processing of the scanned data of the previously injected standard fluid occurs, The WAIT command signal is again supplied, as before, to prevent scanning of the first sample fluid until its injection cycle is completed.

Subsequent injection, scanning, and processing continues in the same manner until all of the samples of all of the groups have been analyzed with reference to the standards corresponding thereto as shown in the flow diagram of FIG. 2.

FIG. 3 shows a flow chart of the steps performed by the automatic injector device 10 in response to the INJ, RUN and WAIT command signals supplied in accordance with Appendix A. For each command, the necessary restoring of appropriate interrupt masks, clearing of input/output flags, reading of the switch register of the 1180 computer, and checking for any errors is performed, all of such steps being known to the art with respect to the Model 1180 computer. Moreover, a suitable software clock is initialized in order to time the delays which are used in the overall operation.

Since each command signal is identified by a specified number, the command number is first determined so that the command which is being supplied is appropriately identified.

Once the INI command, for example; is identified the states of the Level 1 and Level 0 control signals are initialized to their "high" status to prevent any injection operation from being performed until a suitable injection signal (either a RUN on an INJ command signal) is supplied.

If an INJ command is identified as the command being supplied, the Level 1 signal is set to its "low" state and after a suitable delay, fluid from the selected vial is injected into the low pressure flow cell.

If a RUN command is identified as the command being supplied, the Level $\phi$ is set to its "low" state to initiate the injection of fluid from the selected vial into the low pressure flow cell. As mentioned above, the RUN command signal is used when the needle is in its "up" position at the beginning of an overall operation and the INJ command signal is used when the needle is in its "down" position during each subsequent injection operation.

If a WAIT comnand is identified as the command being supplied, the Model 725 device applies a signal which in one state indicates that the injection cycle is completed while in the opposite state indicates that such cycle is not completed. Such signal is supplied to a sensing input of the spectrophotometer, in this case being the Sense 3 input of the Model 1180 computer. If the Sense 3 input, for example, is low, the injection process is not completed and the Model 1180 computer must wait until it has been completed before beginning the next sequential operation. The Sense signal is continued to be monitored and if it is not placed into its "high" state for a suitably selected time period, e.g., about 90 seconds, an error signal is generated signifying a fault in the operation of the injector device.

In summary, the operation of the system of FIG. 1 as described above with reference to the flow charts of FIGS. 2, 2A and 33 provides an effective apparatus for permitting the automatic sequential injection of a plurality of fluid samples into a low pressure flow cell, which samples can be appropriately scanned by a spectrophotometer so that the processed information can be produced automatically without the need for constant operator attention.

What is claimed is:

1. A system for automatically providing a spectrophotometric analysis of a plurality of fluid samples comprising
    a spectrophotometer, including
    a low pressure flow cell for accepting a plurality of successive fluid samples;
    means for scanning fluid samples injected into said flow cell to provide scanned data; and
    means for processing said scanned data;
    automatic injection means, including
        means for storing a plurality of fluid samples without exposure to the atmosphere; and
        means for injecting said stored fluid samples successively at a pressure slightly higher than atmospheric pressure and without exposure to the atmosphere into said low pressure flow cell, said successive samples being retained in said flow cell substantially at atmospheric pressure; and
    control means for controlling the operations of said spectrophotometer and said automatic injection means, said control means including
        means for preventing the scanning of a fluid sample which is being injected into said flow cell until said injection has been completed; and
        means for causing said injecting means to inject the next successive fluid sample into said flow cell and for causing said processing means to process the scanned data of said previously injected fluid sample substantially simultaneously with the injection of said next successive fluid sample.

2. A system in accordance with claim 1 wherein
    the storing means of said automatic injection means is arranged to store one or more groups of fluid samples, each group including a blank fluid, a standard fluid having known characteristics and one or more unknown fluid samples the characteristics of which are not known and are to be compared with the known characteristics of said standard fluid.

3. A system in accordance with claims 1 or 2 wherein said control means further includes
   means for initially preventing the injection of the first fluid sample stored in said storing means until the parameters of said spectrophotometer are set; and
   means operative thereafter for providing successive command signals to said automatic injection means to command said injecting means to inject each successive fluid sample into said flow cell.

4. A system in accordance with claim 3 wherein said storing means of said automatic injection means comprises a plurality of hermetically sealed vials containing the fluid samples and said automatic injection means further includes
   a needle assembly which includes a needle for insertion into each said vial successively for removing the fluid in said vial and supplying said removed fluid to said flow cell, said needle being in a first position when ready for insertion into the vial containing the first fluid sample to be injected into said flow cell and in a second position when ready for insertion into each successive vial, said command signal providing means producing a first command signal when said needle is in its first position and a second command signal when said needle is in its second position.

5. A method for automatically providing a spectrophotometric analysis of a plurality of fluid samples comprising the steps of
   providing successive samples of one or more fluids;
   injecting said successively provided fluid samples at a pressure slightly higher than atmospheric pressure and without exposure to the atmosphere into a low pressure flow cell of a spectrophotometer;
   retaining said successive samples in a said flow cell substantially at atmospheric pressure for scanning thereof by said spectrophotometer to provide scanned data;
   preventing the scanning of each of said successively injected fluid samples until the injection of said corresponding sample into said flow cell has been completed in each case;
   scanning each said successively injected fluid sample only when the injection thereof has been completed to provide scanned data for processing by said spectrophotometer;
   injecting the next successive fluid sample into said flow cell and processing the scanned data of the previously injected fluid sample substantially previously injected fluid sample substantially simultaneously with the injection of said next successive fluid sample.

6. A method in accordance with claim 5 wherein said successive sample providing step includes
   storing a plurality of fluid samples separately without exposure to the atmosphere;
   making the stored fluid samples available for injection into said flow cell in a selected order for scanning thereof.

7. A method in accordance with claim 6 wherein said plurality of stored fluid samples comprise one or more groups thereof, each group including a blank fluid, a standard fluid having known characteristics and one or more unknown fluid samples the characteristics of which are not known and are to be compared with the characteristics of said standard fluid, the order thereof in each group being selected so as to inject the blank fluid first, the standard fluid second, and each of the unknown fluids thereafter.

8. The method of claim 6 and further including the steps of
   setting the parameters of said spectrophotometer; and
   preventing the injection of the initial fluid sample of the first group thereof into said flow cell until all of the parameters have been set.

9. The method of claim 6 wherein said storing step includes the steps of placing each of said fluid samples in a separate hermetically sealed vial; and
   mounting said hermetically sealed vials in said selected order on a movable means so that movement of said movable means makes the fluid stored in each vial available for injection in said selected order.

* * * * *